United States Patent [19]

Lehmann et al.

[11] Patent Number: 5,039,709

[45] Date of Patent: Aug. 13, 1991

[54] ANIPAMIL FOR THE TREATMENT OF CHRONIC RENAL FAILURE

[75] Inventors: Hans D. Lehmann, Hirschberg; Rolf Kretzschmar, Gruenstadt, both of Fed. Rep. of Germany; Laurence Chan, Auroro; Robert W. Schrier, Denver, both of Colo.

[73] Assignee: BASF Aktiengesellschaft, Ludwigshafen, Fed. Rep. of Germany

[21] Appl. No.: 443,198

[22] Filed: Nov. 30, 1989

[51] Int. Cl.$^5$ .............................. A61K 31/075
[52] U.S. Cl. .................................... 514/721
[58] Field of Search ................... 514/523, 721

[56] References Cited

U.S. PATENT DOCUMENTS 4,593,042 10/1985 Liang ............................ 514/523
4,798,811 1/1988 Lehmann et al. ............. 514/159

Primary Examiner—Frederick E. Waddell
Assistant Examiner—Terry Wilson
Attorney, Agent, or Firm—Keil & Weinkauf

[57] ABSTRACT

The use of anipamil and its salts with physiologically tolerated acids for the treatment of chronic renal failure is described.

2 Claims, No Drawings

ANIPAMIL FOR THE TREATMENT OF CHRONIC RENAL FAILURE

The present invention relates to a new use of 1,7-bis(3-methoxyphenyl)-7-cyano-3-methylazanonadecane (anipamil).

EP-A1 64,158 and EP-A1 276,369 disclose various indications for anipamil. Verapamil and gallopamil, which have a similar structure to anipamil, have been described in connection with kidney disorders (DE-A1 1,154,810 and Transplantation 43 (1987) 928, D. C. H. Harris et al., Kidney International 31, (1987), 41–46).

The object of the present invention was to find novel compounds for the treatment of chronic renal failure.

In accordance with this we have now found that anipamil and its physiologically tolerated salts can be used for the treatment of chronic renal failure.

The preparation of anipamil has been described in EP-A1 64,158.

Anipamil can be used in the free form but is expediently employed in the form of a salt with a physiologically tolerated acid. Examples of suitable physiologically tolerated acids are hydrochloric acid, sulfuric acid, phosphoric acid, acetic acid, malonic acid, succinic acid, fumaric acid, maleic acid, citric acid, tartaric acid, lactic acid or sulfamic acid.

Chronic renal failure is a common kidney disorder which results in accumulation in the blood (e.g. creatinine, urea) of substances normally excreted in the urine and, owing to alteration of the filtration function of the kidney; in the excretion of important constituents of blood.

The use, according to the invention, of anipamil leads to a decrease in the concentration of substances such as creatinine or urea in the serum. There is also a distinct improvement in creatinine clearance. One consequence of this is that the kidney dysfunction ceases to progress.

Anipamil or its salts can be administered orally or parenterally in a conventional manner. The dosage depends on the age, condition and weight of the patient and on the mode of administration. As a rule, the daily dose of active substance is from 0.1 to 10 mg/kg of body weight on oral administration and from 0.01 to 1.0 mg/kg of body weight on parenteral administration.

Anipamil and its salts can be used in conventional solid or liquid pharmaceutical forms, for example tablets, powders, capsules, granules, coated tablets, suppositories, solutions or metered aerosols. These can be produced in a conventional manner.

In this connection, anipamil can be processed with the conventional pharmaceutical auxiliaries such as tablet binders, fillers, preservatives, flow-regulators, plasticizers, emulsifiers, solubilizers, retardants or antioxidants. The formulations obtained in this way contain the active substance in an amount of from 0.1 to 99% by weight as a rule.

The beneficial action of anipamil on chronic renal failure was demonstrated in groups of 20 rats with chronic renal failure experimentally induced by 5/6 nephrectomy. The rats received anipamil in daily oral doses of 2 mg/kg of body weight for a period not exceeding 17 weeks or until death. Blood samples were taken from the animals after 4, 8, 12 and, where appropriate, 17 weeks or immediately before obviously imminent death. These were used to determine the serum creatinine and blood urea nitrogen. The systolic blood pressure of the animals was also measured.

The extent of the action was determined by comparison with control animals treated with an antihypertensive (hydralazine) and with placebo. The hydralazine was administered with the drinking water, which contained 80 mg of hydralazine per liter.

In this test, both anipamil and hydralazine had the same good blood pressure-lowering action (see table). Allthough the effect on the blood pressure is the same, that on the kidney function is different: the animals treated with anipamil had a significantly increased excretory function compared with the animals treated with hydralazine, which is evident from the lower concentrations of serum creatinine and blood urea nitrogen and from the considerably improved creatinine clearance. In addition, the animals treated with anipamil lived distinctly longer than those treated with the placebo.

TABLE

| | Duration of treatment (weeks) | N[1] | 1 Anipamil | 2 Hydralazine | 3 control (placebo) |
|---|---|---|---|---|---|
| Systolic blood pressure [mm Hg] | 4 | 11 | 128 | 124 | 180 |
| | 8 | 8 | 126 | 128 | 166 |
| | 12 | 7 | 121 | 120 | 177 |
| Blood urea nitrogen [mg/100 ml] | 4 | 11 | 31 | 86 | 81 |
| | 8 | 8 | 28 | 61 | 87 |
| | 12 | 7 | 29 | 83 | 125 |
| | 17 | 7 | 64 | 114 | 166 |
| Serum creatinine [mg/100 ml] | 4 | 11 | 0.75 | 1.45 | 1.45 |
| | 8 | 8 | 0.90 | 1.40 | 1.73 |
| | 12 | 7 | 0.89 | 1.41 | 2.24 |
| | 17 | 7 | 1.04 | 1.99 | 3.00 |
| Creatinine clearance [μl/min] | 4 | 11 | 1051 | 568 | 686 |
| | 8 | 8 | 896 | 616 | 352 |
| | 12 | 7 | 1041 | 695 | 558 |
| | 17 | 7 | 850 | 343 | 347 |

[1]Number of experimental animals which could be compared

We claim:

1. A method of treating chronic renal failure in a patient suffering therefrom which comprises administering to said patent an effective amount of anipamil or a physiologically tolerated salt of anipamil.

2. The method of claim 1, wherein the patient is treated with the hydrochloride salt of anipamil.

UNITED STATES PATENT AND TRADEMARK OFFICE
CERTIFICATE OF CORRECTION

PATENT NO. : 5,039,709

DATED : August 13, 1991

INVENTOR(S) : Hans LEHMANN et al.

It is certified that error appears in the above-identified patent and that said Letters Patent is hereby corrected as shown below:

On the Title page,

The title should read --The Use of Anipamil For the Treatment of Chronic Renal Failure--

Signed and Sealed this

Fifteenth Day of June, 1993

Attest:

MICHAEL K. KIRK

Attesting Officer

Acting Commissioner of Patents and Trademarks